United States Patent [19]

Drewlow

[11] Patent Number: Plant 7,259

[45] Date of Patent: Jul. 3, 1990

[54] BEGONIA PLANT NAMED FANTASIA

[75] Inventor: Lyndon W. Drewlow, Ashtabula, Ohio

[73] Assignee: Mikkelsens, Inc., Ashtabula, Ohio

[21] Appl. No.: 360,424

[22] Filed: Jun. 2, 1989

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Begonia plant named Fantasia having large, double, slightly ruffled, rose pink flowers; heavily serrated leaf margins, early flowering, long lasting flowers, and the ability to be propagated well from leaf and stem cuttings.

1 Drawing Sheet

The present invention relates to a new and distinctive cultivar of Begonia plant, botanically known as *Begonia hiemalis*×*Begonia fotsch,* and known by the cultivar name Fantasia.

The new cultivar was discovered by me as a seedling from a controlled crossing of tuberous gegonia Mikkelsen seedling 84-652-7, as the seed parent with *B. Socotrana* Mikkelsen seedling 85-1042-4 as the pollen parent.

Asexual reproduction by stem and/or leaf cuttings has reproduced the unique features of the new cultivar through successive propagations.

The following characteristics distinguish the new begonia from both its parents and other Begonias commercially known and used in the floriculture industry. In the comparison, specific references to previously patented cultivars have been made, including Aphrodite Pink (U.S Pat. No. P.P. 3,318), Imke (U.S. Pat. No. P.P. 5,539), and Chantilly (U.S. Pat. No. P.P. 6,434).

1. Fantasia has rose pink flowers, with Aphrodite Pink, Chantilly and Taffeta (not patented) being lighter pink in color, and Imke being more lavender pink in color.

2. Flower size of Fantasia is larger than Taffeta, similar to Aphrodite Pink but not as large as Chantilly and Imke.

3. Fantasia is more double flowered than Aphrodite Pink, and similar to Taffeta, Chantilly and Imke. Margin of tepal is entire on Fantasia and all comparisons except Chantilly, which has serrated margins.

4. Tepals of Fantasia are slightly ruffled, with Chantilly and Aphrodite Pink being more ruffled, and Imke and Taffeta having flat tepals.

5. Fantasia has a spreading pendulous growth habit, with Aphrodite Pink being more pendulous, and Imke, Taffeta and Chantilly having an upright growth habit.

6. Fantasia has darker bright green leaves than Aphrodite Pink which are more yellow green, with Imke, Chantilly and Taffeta all having a duller dark green coloration.

7. The young leaves of Fantasia have a slight reddish cast to the underside which is similar to Aphrodite Pink, with Imke, Taffeta and Chantilly having more red pigmentation on the underside of the leaves.

8. The leaf margins of Fantasia are heavily serrated and the leaf tip is pointed, similar to all comparison cultivars except Aphrodite Pink, which has a rounded leaf tip and a less serrated leaf margin.

9. Stems and leaf petioles of Fantasia have a reddish cast only has a reddish cast in the nodal areas and where the petiole attaches to the leaf.

10. Fantasia has a raceme inflorescence with 3 flowers per raceme. Aphrodite Pink has 5 flower per raceme, while Chantilly, Imke and Taffeta have an umbel type of inflorescence with only a few racemes developing.

11. Early flowering; will flower under long day conditions while Aphrodite Pink will not. Can finish a 25 cm hanging basket in 18 weeks from stem cuttings that are pinched.

12. Flowers are long lasting and do not shatter when shipped.

13. Propagates well from stem and leaf cuttings, and breaks well from a pinch.

14. Good balance between leaf and plant size; dense habit of growth.

15. No female flowers and no pollen in the full double male flowers.

The accompanying colored photograph illustrates in top perspective view the overall appearance of the new cultivar, showing the colors as true as it is reasonably possible to obtain in a colored reproduction of this type. The photograph was taken in December 1988.

The following is a detailed description on my new Begonia cultivar based on plants produced under commercial practices in Ashtabula, Ohio, under greenhouse conditions. Color references are made to The Royal Horticultural Society Colour Chart except where general color terms of ordinary dictionary significance are used.

PARENTAGE

Controlled cross between *B. tuber hybrida* Mikkelsen Seedling No. 84-652-7×B. socotrana Mikkelsen Seedling No. 85-1042-4.

PROPAGATION (A) Type cutting: Leaf cuttings root in 18 days in summer and 24 days in winter at 21° C. at the same temperatures; stems 2–3 cm long root in 16 and 18 days, respectively.

(B) Rooting habit: Abundant, fine, fibrous.

(C) Time for shoot development: For leaf cuttings, 10 weeks in summer to 13 weeks in winter to obtain shoots 4 to 5 cm long in length; for stem cuttings, shoots 5–6 cm long can be obtained in 5 weeks in summer and 6 weeks in winter.

PLANT DESCRIPTION (A) Form: Mounded, semi-spreading; stems becoming pendulous; strong stems can hold flowers without breaking; herbaceous, viborous; suitable for 25 cm hanging basket production; flowers over mounded habit.

(B) Habit of growth: Dense habit without opening between leaves; good basal branching; usually vegetative shoots are formed at the basal nodes and flower shoots at the higher nodes.

(C) Foliage: Leaves simple, alternate, borne on strong petioles 5 mm in diameter on mature leaves.

(1) *Size.*—Can vary greatly with leaf position on plant and number of shoots per plant. Environment can also affect leaf size; 13 to 14 cm across and 14 to 15 cm long when mature.

(2) *Shape.*—Ovate to cordate with lobes overlapping on both mature and immature leaves.

(3) *Texture.*—Leathery, glabrous.

(4) *Margin.*—Serrated with slight red tinge.

(5) *Color.*—Young foliage: Top side, 146 A; under side, 148B. Mature foliage: Top side, 147 A; under side, 148 B, with a slight reddish cast.

(6) *Venation.*—Palmate; 5 to 6 major veins.

FLOWERING DESCRIPTION (A) Flowering habits: Flowering in racemes, with 2–4 flowers per raceme (3 the most common number), with many recemes in bloom at one time. Flowering continues more or less indefinitely.

(B) Natural flowering season: Will flower year around without controlling day length. Plants will flower earlier and more abundantly if subjected to a reduced day length of 12 hours for 3 weeks when day lengths are longer than 12 hours.

(C) Flower buds: 15 mm long and 20 mm wide; just before opening, tepals are entire around margins; color between 50B and 51A just before opening under winter conditions, 47A when immature.

(D) Flowers borne: on strong pendulous peduncles that are reddish green in color and 3–4 mm in diameter.

(E) Quantity: Average of 3 per peduncle, opening in sequence as the raceme develops. Total number of flowers will vary with number of flowering shoots per plant.

(F) Tepals:

(1) *Shape.*—Outer—almost rounded. Inner—heart shaped.

(2) *Color.*—Top side in winter when opening between 50B and 51A, fading to 51 B.

(3) *Number of tepals.*—More than 20.

(4) *Size of tepals.*—Outer 25 mm long, 30 mm wide; inner 10 mm long, 25 mm wide.

(5) *Flower size.*—4 to 4.5 cm in diameter; however, environment can affect size.

(G) Reproductive organs:

(1) *Stamens.*—None as plant is fully double with anthers appearing as petals.

(2) *Pistels.*—None observed to date.

DISEASE RESISTANCE

Fantasia has shown resistance to powdery mildew.

I claim:

1. A new and distinct cultivar of Begonia plant named Fantasia, as described and illustrated.

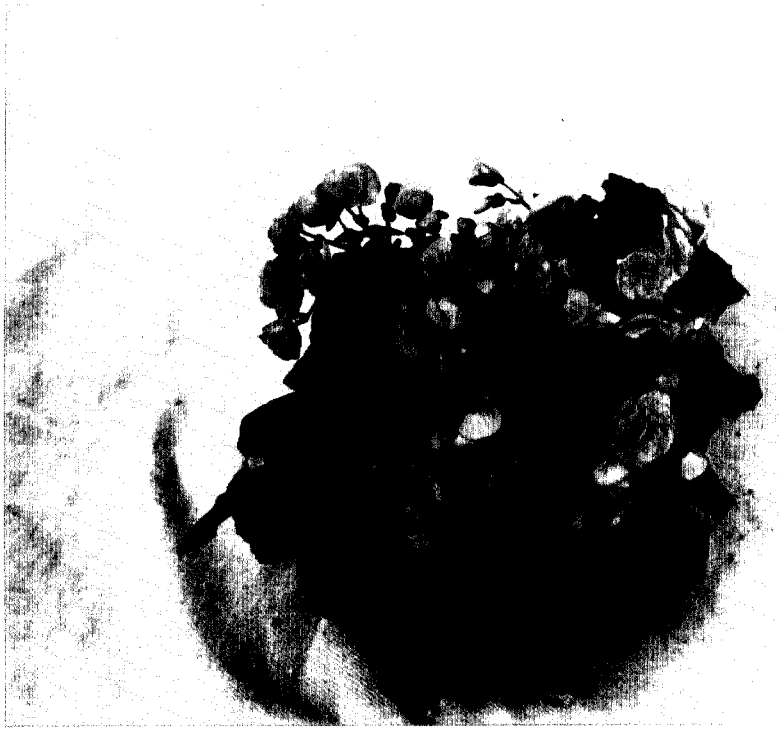

* * * * *